(12) United States Patent
Andersen et al.

(10) Patent No.: US 8,815,541 B2
(45) Date of Patent: Aug. 26, 2014

(54) METHOD FOR MAKING POLYPEPTIDES (75) Inventors: Asser Sloth Andersen, Herlev (DK); Inger Lautrup-Larsen, Virum (DK); Per Noergaard, Humlebaek (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 13/510,363

(22) PCT Filed: Nov. 25, 2010

(86) PCT No.: PCT/EP2010/068178
§ 371 (c)(1),
(2), (4) Date: Jun. 14, 2012

(87) PCT Pub. No.: WO2011/064282
PCT Pub. Date: Jun. 3, 2011

(65) Prior Publication Data
US 2012/0282653 A1    Nov. 8, 2012

Related U.S. Application Data (60) Provisional application No. 61/267,516, filed on Dec. 8, 2009.

(30) Foreign Application Priority Data

Nov. 25, 2009    (EP) .................................. 09177095

(51) Int. Cl.
| | |
|---|---|
| *C12P 21/06* | (2006.01) |
| *C07K 14/575* | (2006.01) |
| *C12P 21/02* | (2006.01) |
| *C12N 15/81* | (2006.01) |
| *C12N 9/60* | (2006.01) |

(52) U.S. Cl.
CPC ............... *C07K 14/575* (2013.01); *C12P 21/02* (2013.01); *C12N 15/81* (2013.01); *C12N 9/60* (2013.01)
USPC ......................................................... 435/69.1

(58) Field of Classification Search
USPC .................................... 435/69.1, 252.3, 320.1
See application file for complete search history.

(56) References Cited

U.S. PATENT DOCUMENTS

| 4,929,553 A | 5/1990 | Bussey et al. |
| 5,367,052 A | 11/1994 | Cooper et al. |

(Continued)

FOREIGN PATENT DOCUMENTS

| EP | 341215 | 5/1989 |
| WO | WO 00/20610 | 4/2000 |

(Continued)

OTHER PUBLICATIONS

Hinnen, A. et al., "Gene Expression in Recombinant Yeast", Gene Expression in Recombinant Microorganisms, 1995, Chapter 3, pp. 121-193.

(Continued)

*Primary Examiner* — Maryam Monshipouri
(74) *Attorney, Agent, or Firm* — Jianjie Hu (57) ABSTRACT

The invention provides an improved method for producing polypeptides with a C-terminal glycine in a yeast transformant being characterized in having a non functional KEX1 gene. The method is in particular well suited to produce polypeptides with an aromatic amino acid residue attached to the C-terminal glycine. The yeast strain may have further non-functional protease genes selected from PEP4, YPS1, MKCI, YPS3, YPS5, YPS6, YPS7, PRB1, STE13 and KEX2.

16 Claims, 1 Drawing Sheet

(56) References Cited

U.S. PATENT DOCUMENTS

| | | | |
|---|---|---|---|
| 6,103,515 A | | 8/2000 | Treichler et al. |
| 6,110,703 A | | 8/2000 | Egel-Mitani et al. |
| 6,124,438 A | * | 9/2000 | Sutcliffe .................... 530/387.9 |
| 2006/0121565 A1 | | 6/2006 | Jonson et al. |

FOREIGN PATENT DOCUMENTS

| WO | WO 2004/003204 | 1/2004 |
|---|---|---|
| WO | WO 2004/027067 | 4/2004 |
| WO | 2007/148345 A2 | 12/2007 |

OTHER PUBLICATIONS

Latchinian-Sadek, L. et al., "Expression, Purification, and Characterization of the Yeast *KEX1* Gene Product, a Polypeptide Precursor Processing Carboxypeptidase", The Journal of Biological Chemistry, 1993, vol. 268, No. 1, pp. 534-540.

Boehm, T. et al., "Disruption of the KEX1 Gene in *Pichia pastoris* Allows Expression of Full-Length Murine and Human Endostatin", Yeast, 1999, vol. 15, No. 7, pp. 563-572.

Copley, K et al. "Expression, processing and secretion of a proteoytically-sensitive insect diuretic hormone by Saccharomyces cerevisiae requires the use of a yeast strain lacking genes encoding the Yap3 and Mkc7 endoproteases found in the secretory pathway." Biochem. J. 1998. vol. 330. pp. 1333-1340.

Heim, J et al. "C-terminal proteolytic degradation of recombinant desulfato-hirudin and its mutants in the yeast Saccharimyces." Eur. J. Biochem. 1994. vol. 226. pp. 341-353.

Merkler, D. "C-Terminal amidated peptides: Production by the in vitro enzymatic amidation of glycine-extended peptides and the importance of the amide to bioactivity." Enzyme Microb. Technol. 1994. vol. 16. pp. 450-456.

\* cited by examiner

SEQUENCE LISTING

```
<160> NUMBER OF SEQ ID NOS: 33

<210> SEQ ID NO 1
<211> LENGTH: 5
<212> TYPE: PRT
<213> ORGANISM: Artificial Sequence
<220> FEATURE:
<223> OTHER INFORMATION: N-terminal extension

<400> SEQUENCE: 1

Glu Glu Ala Glu Lys
1               5

<210> SEQ ID NO 2
<211> LENGTH: 24
<212> TYPE: DNA
<213> ORGANISM: Saccharomyces cerevisiae

<400> SEQUENCE: 2
cccggaaccg aaaaacaatg tgga                                          24

<210> SEQ ID NO 3
<211> LENGTH: 73
<212> TYPE: DNA
<213> ORGANISM: Saccharomyces cerevisiae
```

```
<400> SEQUENCE: 3
agttcagtag tgtgaattaa ataaaacagt cagttcttga tggattgtac cctttaaaga    60
atttatcttt atg                                                      73

<210> SEQ ID NO 4
<211> LENGTH: 42
<212> TYPE: PRT
<213> ORGANISM: Homo sapiens

<400> SEQUENCE: 4

Glu Glu Ala Glu Lys Cys Asn Thr Ala Thr Cys Ala Thr Gln Arg Leu
1               5                   10                  15

Ala Asn Phe Leu Val His Ser Ser Asn Asn Phe Gly Pro Ile Leu Pro
            20                  25                  30

Pro Thr Asn Val Gly Ser Asn Thr Tyr Gly
        35                  40

<210> SEQ ID NO 5
<211> LENGTH: 129
<212> TYPE: DNA
<213> ORGANISM: Homo sapiens

<400> SEQUENCE: 5
gaagaagctg aaaagaatg taatactgct acttgtgcta ctcaaagatt ggctaatttt    60
ttggttcatt cttctaataa ttttggtcca attttgccac caactaatgt tggttctaat   120
acttatggt                                                          129

<210> SEQ ID NO 6
<211> LENGTH: 37
<212> TYPE: PRT
<213> ORGANISM: Homo sapiens

<400> SEQUENCE: 6

Ala Pro Leu Glu Pro Val Tyr Pro Gly Asp Asn Ala Thr Pro Glu Gln
1               5                   10                  15

Met Ala Gln Tyr Ala Ala Asp Leu Arg Lys Tyr Ile Asn Met Leu Thr
            20                  25                  30

Arg Pro Arg Tyr Gly
        35

<210> SEQ ID NO 7
<211> LENGTH: 111
<212> TYPE: DNA
<213> ORGANISM: Artificial Sequence
<220> FEATURE:
<223> OTHER INFORMATION: Synthic DNA

<400> SEQUENCE: 7
gcaccattgg aaccagttta cccaggtgat aacgcaactc cagagcagat ggctcagtat    60
gctgcagatt taagaaagta tataaatatg ttaacaagac caagatatgg t           111

<210> SEQ ID NO 8
<211> LENGTH: 42
<212> TYPE: PRT
<213> ORGANISM: Homo sapiens
```

<400> SEQUENCE: 8

Glu Glu Ala Glu Lys Cys Asn Thr Ala Thr Cys Ala Thr Gln Arg Leu
1               5                   10                  15

Ala Asn Phe Leu Val His Ser Ser Asn Asn Phe Gly Pro Ile Leu Pro
            20                  25                  30

Pro Thr Asn Val Gly Ser Asn Thr Ala Gly
            35                  40

<210> SEQ ID NO 9
<211> LENGTH: 42
<212> TYPE: PRT
<213> ORGANISM: Homo sapiens

<400> SEQUENCE: 9

Glu Glu Ala Glu Lys Cys Asn Thr Ala Thr Cys Ala Thr Gln Arg Leu
1               5                   10                  15

Ala Asn Phe Leu Val His Ser Ser Asn Asn Phe Gly Pro Ile Leu Pro
            20                  25                  30

Pro Thr Asn Val Gly Ser Asn Thr Gly Gly
            35                  40

<210> SEQ ID NO 10
<211> LENGTH: 42
<212> TYPE: PRT
<213> ORGANISM: Homo sapiens

<400> SEQUENCE: 10

Glu Glu Ala Glu Lys Cys Asn Thr Ala Thr Cys Ala Thr Gln Arg Leu
1               5                   10                  15

Ala Asn Phe Leu Val His Ser Ser Asn Asn Phe Gly Pro Ile Leu Pro
            20                  25                  30

Pro Thr Asn Val Gly Ser Asn Thr Phe Gly
            35                  40

<210> SEQ ID NO 11
<211> LENGTH: 42
<212> TYPE: PRT
<213> ORGANISM: Homo sapiens

<400> SEQUENCE: 11

Glu Glu Ala Glu Lys Cys Asn Thr Ala Thr Cys Ala Thr Gln Arg Leu
1               5                   10                  15

Ala Asn Phe Leu Val His Ser Ser Asn Asn Phe Gly Pro Ile Leu Pro
            20                  25                  30

Pro Thr Asn Val Gly Ser Asn Thr Ile Gly
            35                  40

<210> SEQ ID NO 12
<211> LENGTH: 42
<212> TYPE: PRT
<213> ORGANISM: Homo sapiens

<400> SEQUENCE: 12

Glu Glu Ala Glu Lys Cys Asn Thr Ala Thr Cys Ala Thr Gln Arg Leu
1               5                   10                  15

Ala Asn Phe Leu Val His Ser Ser Asn Asn Phe Gly Pro Ile Leu Pro
            20                  25                  30

Pro Thr Asn Val Gly Ser Asn Thr Met Gly
            35                  40

<210> SEQ ID NO 13
<211> LENGTH: 42
<212> TYPE: PRT
<213> ORGANISM: Homo sapiens

<400> SEQUENCE: 13

Glu Glu Ala Glu Lys Cys Asn Thr Ala Thr Cys Ala Thr Gln Arg Leu
1               5                   10                  15

Ala Asn Phe Leu Val His Ser Ser Asn Asn Phe Gly Pro Ile Leu Pro
            20                  25                  30

Pro Thr Asn Val Gly Ser Asn Thr Ser Gly
        35                  40

<210> SEQ ID NO 14
<211> LENGTH: 42
<212> TYPE: PRT
<213> ORGANISM: Homo sapiens

<400> SEQUENCE: 14

Glu Glu Ala Glu Lys Cys Asn Thr Ala Thr Cys Ala Thr Gln Arg Leu
1               5                   10                  15

Ala Asn Phe Leu Val His Ser Ser Asn Asn Phe Gly Pro Ile Leu Pro
            20                  25                  30

Pro Thr Asn Val Gly Ser Asn Thr Pro Gly
        35                  40

<210> SEQ ID NO 15
<211> LENGTH: 42
<212> TYPE: PRT
<213> ORGANISM: Homo sapiens

<400> SEQUENCE: 15

Glu Glu Ala Glu Lys Cys Asn Thr Ala Thr Cys Ala Thr Gln Arg Leu
1               5                   10                  15

Ala Asn Phe Leu Val His Ser Ser Asn Asn Phe Gly Pro Ile Leu Pro
            20                  25                  30

Pro Thr Asn Val Gly Ser Asn Thr Thr Gly
        35                  40

<210> SEQ ID NO 16
<211> LENGTH: 42
<212> TYPE: PRT
<213> ORGANISM: Homo sapiens

<400> SEQUENCE: 16

Glu Glu Ala Glu Lys Cys Asn Thr Ala Thr Cys Ala Thr Gln Arg Leu
1               5                   10                  15

Ala Asn Phe Leu Val His Ser Ser Asn Asn Phe Gly Pro Ile Leu Pro
            20                  25                  30

Pro Thr Asn Val Gly Ser Asn Thr Trp Gly
        35                  40

<210> SEQ ID NO 17
<211> LENGTH: 42
<212> TYPE: PRT
<213> ORGANISM: Homo sapiens

```
<400> SEQUENCE: 17

Glu Glu Ala Glu Lys Cys Asn Thr Ala Thr Cys Ala Thr Gln Arg Leu
1               5                   10                  15

Ala Asn Phe Leu Val His Ser Ser Asn Asn Phe Gly Pro Ile Leu Pro
            20                  25                  30

Pro Thr Asn Val Gly Ser Asn Thr Arg Gly
        35                  40

<210> SEQ ID NO 18
<211> LENGTH: 42
<212> TYPE: PRT
<213> ORGANISM: Homo sapiens

<400> SEQUENCE: 18

Glu Glu Ala Glu Lys Cys Asn Thr Ala Thr Cys Ala Thr Gln Arg Leu
1               5                   10                  15

Ala Asn Phe Leu Val His Ser Ser Asn Asn Phe Gly Pro Ile Leu Pro
            20                  25                  30

Pro Thr Asn Val Gly Ser Asn Thr Leu Gly
        35                  40

<210> SEQ ID NO 19
<211> LENGTH: 42
<212> TYPE: PRT
<213> ORGANISM: Homo sapiens

<400> SEQUENCE: 19

Glu Glu Ala Glu Lys Cys Asn Thr Ala Thr Cys Ala Thr Gln Arg Leu
1               5                   10                  15

Ala Asn Phe Leu Val His Ser Ser Asn Asn Phe Gly Pro Ile Leu Pro
            20                  25                  30

Pro Thr Asn Val Gly Ser Asn Thr Gln Gly
        35                  40

<210> SEQ ID NO 20
<211> LENGTH: 42
<212> TYPE: PRT
<213> ORGANISM: Homo sapiens

<400> SEQUENCE: 20

Glu Glu Ala Glu Lys Cys Asn Thr Ala Thr Cys Ala Thr Gln Arg Leu
1               5                   10                  15

Ala Asn Phe Leu Val His Ser Ser Asn Asn Phe Gly Pro Ile Leu Pro
            20                  25                  30

Pro Thr Asn Val Gly Ser Asn Thr Asn Gly
        35                  40

<210> SEQ ID NO 21
<211> LENGTH: 129
<212> TYPE: DNA
<213> ORGANISM: Homo sapiens

<400> SEQUENCE: 21
gaagaagctg aaaagaatg taatactgct acttgtgcta ctcaaagatt ggctaatttt      60
ttggttcatt cttctaataa ttttggtcca attttgccac caactaatgt tggttctaat    120
actgctggt                                                            129
```

<210> SEQ ID NO 22
<211> LENGTH: 129
<212> TYPE: DNA
<213> ORGANISM: Homo sapiens

<400> SEQUENCE: 22

```
gaagaagctg aaaaagaatg taatactgct acttgtgcta ctcaaagatt ggctaatttt      60
ttggttcatt cttctaataa ttttggtcca attttgccac caactaatgt tggttctaat     120
actggtggt                                                             129
```

<210> SEQ ID NO 23
<211> LENGTH: 129
<212> TYPE: DNA
<213> ORGANISM: Homo sapiens

<400> SEQUENCE: 23

```
gaagaagctg aaaaagaatg taatactgct acttgtgcta ctcaaagatt ggctaatttt      60
ttggttcatt cttctaataa ttttggtcca attttgccac caactaatgt tggttctaat     120
acttttggt                                                             129
```

<210> SEQ ID NO 24
<211> LENGTH: 129
<212> TYPE: DNA
<213> ORGANISM: Homo sapiens

<400> SEQUENCE: 24

```
gaagaagctg aaaaagaatg taatactgct acttgtgcta ctcaaagatt ggctaatttt      60
ttggttcatt cttctaataa ttttggtcca attttgccac caactaatgt tggttctaat     120
actattggt                                                             129
```

<210> SEQ ID NO 25
<211> LENGTH: 129
<212> TYPE: DNA
<213> ORGANISM: Homo sapiens

<400> SEQUENCE: 25

```
gaagaagctg aaaaagaatg taatactgct acttgtgcta ctcaaagatt ggctaatttt      60
ttggttcatt cttctaataa ttttggtcca attttgccac caactaatgt tggttctaat     120
actatgggt                                                             129
```

<210> SEQ ID NO 26
<211> LENGTH: 129
<212> TYPE: DNA
<213> ORGANISM: Homo sapiens

<400> SEQUENCE: 26

```
gaagaagctg aaaaagaatg taatactgct acttgtgcta ctcaaagatt ggctaatttt      60
ttggttcatt cttctaataa ttttggtcca attttgccac caactaatgt tggttctaat     120
acttctggt                                                             129
```

<210> SEQ ID NO 27
<211> LENGTH: 129
<212> TYPE: DNA
<213> ORGANISM: Homo sapiens

<400> SEQUENCE: 27
gaagaagctg aaaaagaatg taatactgct acttgtgcta ctcaaagatt ggctaatttt    60
ttggttcatt cttctaataa ttttggtcca attttgccac caactaatgt tggttctaat   120
actcctggt                                                           129

<210> SEQ ID NO 28
<211> LENGTH: 129
<212> TYPE: DNA
<213> ORGANISM: Homo sapiens

<400> SEQUENCE: 28
gaagaagctg aaaaagaatg taatactgct acttgtgcta ctcaaagatt ggctaatttt    60
ttggttcatt cttctaataa ttttggtcca attttgccac caactaatgt tggttctaat   120
actactggt                                                           129

<210> SEQ ID NO 29
<211> LENGTH: 129
<212> TYPE: DNA
<213> ORGANISM: Homo sapiens

<400> SEQUENCE: 29
gaagaagctg aaaaagaatg taatactgct acttgtgcta ctcaaagatt ggctaatttt    60
ttggttcatt cttctaataa ttttggtcca attttgccac caactaatgt tggttctaat   120
acttggggt                                                           129

<210> SEQ ID NO 30
<211> LENGTH: 129
<212> TYPE: DNA
<213> ORGANISM: Homo sapiens

<400> SEQUENCE: 30
gaagaagctg aaaaagaatg taatactgct acttgtgcta ctcaaagatt ggctaatttt    60
ttggttcatt cttctaataa ttttggtcca attttgccac caactaatgt tggttctaat   120
actagaggt                                                           129

<210> SEQ ID NO 31
<211> LENGTH: 129
<212> TYPE: DNA
<213> ORGANISM: Homo sapiens

<400> SEQUENCE: 31
gaagaagctg aaaaagaatg taatactgct acttgtgcta ctcaaagatt ggctaatttt    60
ttggttcatt cttctaataa ttttggtcca attttgccac caactaatgt tggttctaat   120
actcttggt                                                           129

<210> SEQ ID NO 32
<211> LENGTH: 129
<212> TYPE: DNA
<213> ORGANISM: Homo sapiens

<400> SEQUENCE: 32
gaagaagctg aaaaagaatg taatactgct acttgtgcta ctcaaagatt ggctaatttt    60
ttggttcatt cttctaataa ttttggtcca attttgccac caactaatgt tggttctaat   120
actcaaggt                                                           129

```
<210> SEQ ID NO 33
<211> LENGTH: 129
<212> TYPE: DNA
<213> ORGANISM: Homo sapiens

<400> SEQUENCE: 33
gaagaagctg aaaaagaatg taatactgct acttgtgcta ctcaaagatt ggctaattt      60 ttggttcatt cttctaataa ttttggtcca attttgccac caactaatgt tggttctaat    120
actaatggt                                                            129
```

METHOD FOR MAKING POLYPEPTIDES

CROSS-REFERENCE TO RELATED APPLICATIONS

This application is a 35 U.S.C. §371 national stage application of International Patent Application PCT/EP2010/068178 (published as WO 2011/064282 A1), filed Nov. 25, 2010, which claimed priority of European Patent Application 09177095.8, filed Nov. 25, 2009; this application further claims priority under 35 U.S.C. §119 of U.S. Provisional Application 61/267,516, filed Dec. 8, 2009.

FIELD OF THE INVENTION

The present invention is related to a process for making polypeptides in a genetically modified yeast strain.

INCORPORATION-BY-REFERENCE OF THE SEQUENCE LISTING

In accordance with 37 C.F.R. §1.52(e)(5), Applicants enclose herewith the Sequence Listing for the above-captioned application entitled "SEQUENCE LISTING", created on Apr. 17, 2012. The Sequence Listing is made up of 11,699 bytes, and the information contained in the attached "SEQUENCE LISTING" is identical to the information in the specification as originally filed. No new matter is added.

BACKGROUND OF THE INVENTION

Expression of heterologous proteins in yeast after transformation of yeast cells with suitable expression vectors comprising DNA sequences coding for said proteins has been successful for many species of polypeptides, such as insulin precursors, glucagon, glucagon like peptides and their functional analogues.

However, it is often found that the expression product is a heterogeneous mixture of species of the desired polypeptide precursor having different amino acid chain lengths. This is because yeast produces a number of proteolytic enzymes being responsible for processing of larger precursor molecules to release the mature polypeptide. A number of proteases including the PEP4 and KEX1 gene products are responsible for such yeast protein degradation.

The use of KEX1 disrupted strains for expression of recombinant proteins have been described earlier. Thus EP341215 and U.S. Pat. No. 6,103,515 describe use of a yeast strain which lacks KEX1 for production of peptides which bear no basic C-terminal amino acid e.g. hANP, EGF, connective tissue activating peptide-III hirudin and hirudin variants.

More than half of the known neural and endocrine peptides are α-amidated and in most cases, this structural feature is essential for receptor recognition, signal transduction, and thus, biologic function. The α-amidation is derived from a C-terminal glycine that is enzymatically converted to an amide.

An α-amidated peptide may be produced directly in the production cell if the cell has the necessary machinery for in vivo α-amidation. However, some organisms including yeast are not capable of making the α-amidation because they do not express the necessary enzyme for in vivo α-amidation and therefore peptides produced by the cell have to be α-amidated by a subsequent in vitro step.

If yeast is used as the recombinant production cell one solution is to produce a precursor polypeptide with a C-terminal glycine which is then in a subsequent in vitro process converted to the α-amidated peptide using an α-amidating enzyme (D. J. Merkler (1994). C-Terminal amidated peptides: Production by the in vitro enzymatic amidation of glycine extended peptides and the importance of the amide to bioactivity. Enzyme Microb. Technol.: 16(450-456).

Surprisingly however, the inventors of the present invention have discovered that the C-terminal glycine is cleaved off from a number of peptides expressed from *Saccharomyces cerevisiae* making the subsequent conversion to an α-amidated peptide impossible.

The present invention offers a solution to this problem by using a genetically modified yeast strain which will not cleave off the C-terminal glycine residue.

SUMMARY OF THE INVENTION

In one aspect the present invention is related to a method for making a polypeptide with a C-terminal Gly in yeast, wherein the yeast strain has a non functional KEX1 gene.

The KEX1 gene can be made non functional by use of well known techniques. Thus in one embodiment the KEX1 gene is simply deleted and in another embodiment the KEX1 gene is made non functional by site specific mutation e.g. by or homologous recombination.

In one embodiment the invention is related to a method for making a polypeptide in a yeast strain having a non functional KEX1 gene, wherein, the polypeptide as its C-terminal amino acid residue has a glycine, and wherein the method comprises the following steps a) culturing the yeast strain comprising a DNA sequence encoding the polypeptide under conditions for expressing the polypeptide in the yeast strain and b) isolation of the expressed polypeptide.

The expressed polypeptide may be isolated either from the cell culture or from the yeast cells dependent on whether the expressed polypeptide is secreted from the yeast cell.

The C-terminal glycine is especially labile when the penultimate amino acid from the C-terminal end is one of the following amino acid residues: Tyr, Phe, Met, Leu, Trp, Ala, Ile and Arg. Thus, in one embodiment the penultimate amino acid from the C-terminal end is Tyr, Phe, Met, Leu, Trp, Ala, Ile or Arg.

With "penultimate amino acid from the C-terminal end" is meant the amino acid residue attached to the N-terminal end of the C-terminal amino acid residue which in this case is a glycine recidue.

In particular the C-terminal glycine is more labile when the penultimate amino acid from the C-terminal end is a hydrophobic amino acid residue and in particular an aromatic amino acid residue. Thus, in a further embodiment the amino acid residue next to the C-terminal Gly is Tyr, Trp, Phe, Val, Leu, Ile or Met and in a further embodiment the amino acid residue attached to the C-terminal Gly is Val, Leu, Ile or Met and in a further embodiment the amino acid residue attached to the C-terminal Gly is Tyr, Phe or Trp.

In a still further embodiment the amino acid residue attached to the C-terminal Gly is Tyr.

The yeast strain may have further non functional protease genes in addition to the non functional KEX1 gene. Thus, in one embodiment the yeast strain may have at least one further non-functional protease gene selected from the group consisting of PEP4, YPS1, MKC7, YPS3, YPS5, YPS6, YPS7, PRB1, STE13 and KEX2.

The size of the polypeptide in question may also be of relevance and in a further embodiment the polypeptide has from about 25 to about 75 amino acid residues in the backbone. In a further embodiment the polypeptide has from about 25 to about 60 amino acid residues in the backbone and in a still further embodiment the polypeptide has from about 25 to about 45 amino acid residues in the backbone.

The yeast strain may be any yeast strain which is capable of expressing and secreting foreign DNA. However, in one embodiment the yeast strain is a *Saccharomyces cerevisiae* strain.

The method of the invention may comprise an additional enzymatic conversion of the expressed and secreted polypeptide. Thus in one embodiment of the invention the expressed and secreted polypeptide with a C-terminal Gly is converted into an amide by enzymatic conversion with an α-amidation enzyme in a further in vitro step.

DETAILED DESCRIPTION OF THE INVENTION

Expression of peptides with a C-terminal glycine in *S. cerevisiae* strain has as mentioned been proven to be problematic as the glycine is efficiently cleaved off-especially if the penultimate amino acid from the C-terminal end is a tyrosine as in PP (pancreatic polypeptide), PYY and amylin and according to the present invention it has been found out that in yeast strains the responsible protease for cleavage of the C-terminal glycine is the Kex1p protease.

With "Kex1" or "Kex1p" is meant a serine carboxypeptidase that preferentially catalyzes removal of C-terminal lysyl and/or arginyl residues (Shilton B H, Thomas D Y, Cygler M 1997 Crystal structure of Kex1 deltap, a prohormone-processing carboxypeptidase from *Sacharomyces cerevisiae*. Biochemistry 36: 9002-9012). Kex1p or carboxypeptidase yscα is a membrane-associated exopeptidase and plays an important role in the maturation of killer factor and mating factor α in yeast. The enzyme is highly specific to C-terminal basic amino acid residues (Arg and Lys). The specificity of the KEX1 enzyme has further been investigated by a.o. Heim et al, Eur. J. Biochem 226: 341-353 (1994)) with desulfato-hirudin and its mutants as model substrates.

This invention describes the use of a yeast strain with a non functional KEX1 gene to express small peptides that have a C-terminal glycine amino acid residue. This glycine has been shown to be very labile to cleavage by Kex1p, making it difficult to express these peptides efficiently in yeast.

With "small peptides" in this context is meant peptides with up to about 75 amino acid residues. In one embodiment the peptides have up to about 60 amino acid residues and in a further embodiment the peptides have up to about 50 amino acid residues. In a still further embodiment the peptides have between about 25 and about 45 amino acid residues.

Illustrative, non limiting examples of peptides which can be produced according to the present invention are amylin, amylin analogues, PP and PP analogues, PYY and PYY analogues, GLP-1 and GLP1 analogues, oxytocin, vasopressin, calcitonin, gastrin, NPY, FMRF amide, secretin, GFHR, CRF, neurokinin A, gastrin releasing peptide and α-MSH.

In one embodiment the peptide which can be produced is selected from the group of peptides which have an aromatic amino acid residue linked to the glycine residue. Thus in one embodiment the peptide is selected from the group consisting of gastrin, NPY, FMRF amide and amylin and analogues thereof.

The expression "polypeptide" is meant to cover "peptides" and "proteins" as well. By "analogue" as used herein is meant a polypeptide which has a molecular structure which formally can be derived from the structure of a naturally occurring polypeptide by deleting and/or exchanging at least one amino acid residue occurring in the naturally occurring polypeptide. The added and/or exchanged amino acid residues can either be codable amino acid residues or other naturally occurring residues or purely synthetic amino acid residues.

The activity of a protease can be eliminated by disruption of the host gene encoding the protease, thereby generating a non-reverting strain missing all or part of the gene for the protease including regulatory and/or coding regions, or, alternatively, the activity can be reduced or eliminated by classical mutagenesis procedures or by the introduction of specific point mutations. Disruption of the gene encoding for the Kex1p protease using classical techniques relies on homologous recombination, where two similar or identical strands of DNA exchange nucleotide sequences. This allows direction of the recombination event specifically to the KEX1 locus, whereby the KEX1 open reading frame is exchanged with a marker gene, used for selection of the correct deletion (Rothstein R. Targeting, disruption, replacement, and allele rescue: integrative DNA transformation in yeast. 1991. Methods Enzymol. 194:281-301). In one mode of this, the yeast strain is transformed with a linear DNA fragment (coming from a plasmid or generated by PCR) consisting of the marker gene flanked by DNA sequences homologous to the DNA sequences flanking the KEX1 gene. Successful integration will replace the KEX1 gene with the marker gene which can be selected for. Suitable markers are auxotrophic markers such as for instance URA3, HIS3, LEU2, TRP1 or dominant antibiotic markers that give resistance towards G418, hygromycin etc.

Other methods which may be suitable for down regulation of the protease activity include the introduction of antisense and/or ribozyme constructs in the yeast, e.g. Atkins et al. (Antisense and Development 5: 295-305, 1995) and Nasr et al. (Mol. Gen Genet 249: 51-57, 1995). One useful methods of disrupting the KEX1 gene in the yeast strain are described by Rothstein (Method in Enzymol, 194: 281-301, 1991).

Depending on the desired end product, the yeast host cell may be further genetically manipulated. As an example, one or more further protease gene can be made nonfunctional. Examples of such protease genes are PEP4, YPS1, MKC7 (YPS2), YPS3(YPS4), YPS5, YPS6, YPS7, PRB1, STE13 and KEX2. This may be necessary to avoid additional degradation of the expressed peptide.

In one embodiment the yeast strain has a knock-out of the KEX1 gene and a single of the protease genes selected from the following group PEP4, YPS1, MKC7(YPS2), YPS3 (YPS4), YPS5, YPS6, YPS7, PRB1, STE13 and KEX2.

In another embodiment the yeast strain has a knock-out of the KEX1 gene and two of the protease genes selected from the following group PEP4, YPS1, MKC7(YPS2), YPS3 (YPS4), YPS5, YPS6, YPS7, PRB1, STE13 and KEX2.

In another embodiment the yeast strain has a knock-out of the KEX1 gene and three of the protease genes selected from the following group PEP4, YPS1, MKC7(YPS2), YPS3 (YPS4), YPS5, YPS6, YPS7, PRB1, STE13 and KEX2.

In another embodiment the yeast strain has a knock-out of the KEX1 gene and four of the protease genes selected from the following group PEP4, YPS1, MKC7(YPS2), YPS3 (YPS4), YPS5, YPS6, YPS7, PRB1, STE13 and KEX2.

In one embodiment the KEX1 and the PEP4 genes are made non functional. Such yeast strain is particular suitable for expression of amyl in, PP and PYY and analogues thereof with a C-terminal glycine.

In another embodiment the yeast strain has a disrupted KEX1 gene and a disrupted yeast aspartyl protease 3 (Yap3p) gene (YPS1). Disruption of the yeast aspartyl protease 3 (Yap3p) gene is described in WO 95/23857 for production of recombinant human albumin (rHA) and in U.S. Pat. No. 6,110,703 describing production of short chain polypeptides.

Thus a further embodiment of the present invention includes a yeast strain which has a knock-out of both the KEX1 and the YAP3IYPS1 gene.

With the expression "knock-out" is meant that the gene has either been totally deleted or has been made non-functional as described earlier.

The method according to the present invention results in non degraded peptides with an intact C-terminal. This is of a high commercial value as the production of a homogeneous product will reduce the purification costs significantly.

In a further aspect the present invention is related to a process for making C-terminal amidated peptides comprising the following steps: a) culturing a yeast strain having a non functional KEX1 gene and comprising a DNA sequence encoding a polypeptide with a C-terminal Gly under conditions for expressing the polypeptide in the yeast strain, b) in vitro α-amidation of the expressed polypeptide from step a) and b) isolation and purification of the C-terminally amidated peptide.

In another aspect the invention provides a culture of yeast cells having a non functional KEX1 gene comprising a polyneucleotide sequence encoding a polypeptide with a C-terminal Gly residue said polynucleotide sequence or DNA sequence being operably linked to a polynucleotide sequence or DNA sequence encoding a yeast promoter and a leader sequence (pro sequence or prepro sequence) and/or other polynuceotide sequences or DNA sequences that are necessary for said polypeptide to be expressed in and secreted from the yeast.

The DNA encoding the polypeptide in question may be joined to a wide variety of other DNA sequences for introduction into an appropriate host. The companion DNA will depend upon the nature of the host, the manner of the introduction of the DNA into the host, and whether episomal maintenance or integration on host chromosome(s) is desired.

Generally, the DNA is inserted into an expression vector, such as a plasmid, in proper orientation and correct reading frame for expression. The vector is then introduced into the host through standard techniques and, generally, it will be necessary to select for transformed host cells.

In the vector the polynucleotide sequence or the DNA sequence is operably linked to a polynucleotide sequence or DNA sequence encoding a yeast promoter and a leader sequence (pro sequence or prepro sequence) and/or other polynucleotide sequences or DNA sequences that are necessary for said polypeptide to be expressed in and secreted from the yeast.

If integration is desired, the DNA is inserted into an yeast integration plasmid vector, such as pJJ215, pJJ250, pJJ236, pJJ248, pJJ242 (Jones & Prakash, Yeast 6: 363,1990) or pDP6 (Fleig et al. Gene 46:237, 1986), in proper orientation and correct reading frame for expression, which is flanked with homologous sequences of any non-essential yeast genes, transposon sequence or ribosomal genes. Preferably the flanking sequences are yeast protease genes or genes used as a selective marker. The DNA is then integrated on host chromosome(s) by homologous recombination occurred in the flanking sequences, by using standard techniques shown in Rothstein (Method in Enzymol, 194: 281-301, 1991) and Cregg et al. (Bio/Technol. 11:905-910, 1993).

Host cells that have been transformed by the recombinant DNA of the invention are then cultured for a sufficient time and under appropriate conditions known to those skilled in the art in view of the teachings disclosed herein to permit the expression and secretion of the polypeptides to be produced according to the method of the invention.

Useful yeast plasmid vectors include the POT (Kjeldsen et al. Gene 170: 107-112, 1996) and YEp13, YEp24 (Rose and Broach, Methods in Enzymol. 185: 234-279, 1990), and pG plasmids (Schena et al. Methods in Enzymol. 194: 289-398, 1991).

Methods for the transformation of *S. cerevisiae* include the spheroplast transformation, lithium acetate transformation, and electroporation, cf. Methods in Enzymol. Vol. 194 (1991). Pereferably the transformation is as described in the examples herein.

Suitable promoters for *S. cerevisiae* include the MFα1 promoter, galactose inducible promoters such as GAL1, GAL7 and GAL10 promoters, glycolytic enzyme promoters including TPI and PGK promoters, TRP1 promoter, CYCI promoter, CUP1 promoter, PHO5 promoter, ADH1 promoter, and HSP promoter. A suitable promoter in the genus *Pichia* is the AOXI (methanol utilisation) promoter.

The transcription terminal signal is preferably the 3' flanking sequence of a eukaryotic gene which contains proper signal for transcription termination and polyadenylation. Suitable 3' flanking sequences may, e.g. be those of the gene naturally linked to the expression control sequence used, i.e. corresponding to the promoter.

The DNA constructs that are used for providing secretory expression of the desired polypeptide comprise a DNA sequence that includes a leader sequence linked to the polypeptide by a yeast processing signal. The leader sequence contains a signal peptide ("pre-sequence") for protein translocation across the endoplasmic reticulum and optionally contains an additional sequence ("pro-sequence"), which may or may not be cleaved within yeast cells before the polypeptide is released into the surrounding medium. Useful leaders are the signal peptide of mouse α-amylase, *S. cerevisiae* MFα1, YAP3, BAR1, HSP150 and *S. kluyveri* MFα signal peptides and prepro-sequences of *S. cerevisiae* MFα1, YAP3, PRC, HSP150, and *S. kluyveri* MFα and synthetic leader sequences described in WO 92/11378, WO 90/10075 and WO 95/34666. Furthermore, the polypeptides to be produced according to the method of the invention may be provided with an N-terminal extension as described in WO 95/35384.

The DNA sequence encoding the desired peptide may be of genomic or cDNA origin, for instance be obtained by preparing a genomic or cDNA library and screening for DNA sequences coding for all or part of the polypeptide by hybridization using synthetic oligonucleotide probes in accordance with standard techniques (see, for example, Sambrook, J, Fritsch, E F and Maniatis, T, *Molecular Cloning: A Laboratory Manual*, Cold Spring Harbor Laboratory Press, New York, 1989). The DNA sequence encoding the polypeptide may also be prepared synthetically by established standard methods, e.g. the phosphoamidite method described by Beaucage and Caruthers, *Tetrahedron Letters* 22 (1981), 1859-1869, or the method described by Matthes et al., *EMBO Journal* 3 (1984), 801-805. The DNA sequence may also be prepared by polymerase chain reaction using specific primers, for instance as described in U.S. Pat. No. 4,683,202 or Saiki et al., *Science* 239 (1988), 487-491.

The yeast host cell into which the DNA sequence or the recombinant vector is introduced may be any yeast cell which is capable of expressing the popypeptide and includes *Saccharomyces* spp. or *Schizosaccharomyces* spp., in particular strains of *Saccharomyces cerevisiae* or *Saccharomyces kluyveri*. Further examples of suitable yeast cells are strains of *Kluyveromyces*, such as *K. lactis, Hansenula*, e.g. *H. polymorphs*, or *Pichia*, e.g. *P. pastoris* (cf. Gleeson et al., J. Gen. Microbiol. 132, 1986, pp. 3459-3465; U.S. Pat. No. 4,882, 279).

Methods for transforming yeast cells with heterologous DNA and producing heterologous polypeptides there from are described, e.g. in U.S. Pat. No. 4,599,311, U.S. Pat. No. 4,931,373, U.S. Pat. Nos. 4,870,008, 5,037,743, and U.S. Pat. No. 4,845,075. Transformed cells are selected by a phenotype determined by a selectable marker, commonly drug resistance or the ability to grow in the absence of a particular nutrient, e.g. leucine. A preferred vector for use in yeast is the POT1 vector disclosed in U.S. Pat. No. 4,931,373. "POT" is the *Schizosaccharomyces pombe* triose phosphate isomerase gene, and "TPI1" is the *S. cerevisiae* triose phosphate isomerise gene.

The expression "a codable amino acid" or "a codable amino acid residue" is used to indicate an amino acid or amino acid residue which can be coded for by a triplet ("codon") of nucleotides.

In the present context the three-letter or one-letter indications of the amino acids have been used in their conventional meaning as indicated in the following table. Unless indicated explicitly, the amino acids mentioned herein are L-amino acids. Further, the left and right ends of an amino acid sequence of a peptide are, respectively, the N- and C-termini unless otherwise specified.

The present invention is described in further detain in the following examples which are not in any way intended to limit the scope of the invention as claimed. The attached Figures are meant to be considered as integral parts of the specification and description of the invention. All references cited are herein specifically incorporated by reference for all that is described therein.

The following embodiments are covered by the present invention:

Embodiment 1: Method for making a polypeptide in a yeast strain having a non functional KEX1 gene, wherein, the polypeptide as its C-terminal amino acid residue has a glycine, and wherein the method comprises the following steps
a) culturing the yeast strain comprising a DNA sequence encoding the polypeptide under conditions for expressing the polypeptide in the yeast strain and
b) isolation of the expressed polypeptide;

Embodiment 2: Method according to embodiment 1, wherein the polypeptide is isolated from the culture medium;

Embodiment 3: Method according to embodiment 1-2, wherein the amino acid residue attached to the C-terminal Gly is from the group consisting of Tyr, Phe, Met, Leu, Trp, Ala, Ile and Arg;

Embodiment 4: Method according to embodiment 3, wherein the amino acid residue attached to the C-terminal Gly is Tyr, Trp, Phe, Val, Leu, Ile and Met;

Embodiment 5: Method according to embodiment 3, wherein the amino acid residue attached to the C-terminal Gly is Val, Leu, Ile and Met;

Embodiment 6: Method according to embodiment 3, wherein the amino acid residue attached to the C-terminal Gly is Tyr, Trp and Phe;

Embodiment 7: Method according to embodiment 6, wherein the amino acid residue attached to the C-terminal Gly is Tyr;

Embodiment 8: Method according to any of embodiment 1-7, wherein the yeast strain has at least one further non-functional protease gene selected from the group consisting of PEP4, YPS1, MKC7, YPS3, YPS5, YPS6, YPS7, PRB1, STE13 and KEX2;

Embodiment 9: Method according to embodiment 8, wherein the yeast strain has a further non-functional protease gene selected from the group consisting of PEP4, YPS1 and MKC7;

Embodiment 10: Method according to embodiment 8, wherein the yeast strain has a further non-functional protease gene selected from the group consisting of PEP4, YPS1 and YPS3;

Embodiment 11: Method according to embodiment 8, wherein the yeast strain has a further non-functional protease gene selected from the group consisting of PEP4, YPS3 and MKC7;

Embodiment 12: Method according to embodiment 8, wherein the yeast strain has a further non-functional protease gene selected from the group consisting of PEP4 and YPS1;

Embodiment 13: Method according to embodiment 8, wherein the yeast strain has a further non-functional protease gene selected from the group consisting of PEP4, and YPS3;

Embodiment 14: Method according to embodiment 8, wherein the yeast strain has a further non-functional protease gene selected from the group consisting of PEP4 and MKC7;

Embodiment 15: Method according to embodiment 8, wherein the yeast strain has a further non-functional protease gene selected from the group consisting of YPS3, YPS1 and MKC7;

Embodiment 16: Method according to embodiment 8, wherein the yeast strain has a further non-functional protease gene selected from the group consisting of YPS3 and YPS1;

Embodiment 17: Method according to embodiment wherein the yeast strain has a further non-functional protease gene selected from the group consisting of YPS3 and MKC7;

Embodiment 18: Method according to embodiment 8, wherein the yeast strain has a further non-functional protease gene selected from the group consisting of PEP4 and YPS5;

Embodiment 19: Method according to embodiment 8, wherein the yeast strain has a further non-functional protease gene selected from the group consisting of PEP4 and YPS6; Embodiment 20: Method according to embodiment 8, wherein the yeast strain has a further nonfunctional protease gene selected from the group consisting of PEP4 and YPS7;

Embodiment 21: Method according to embodiment 8, wherein the yeast strain has a further non-functional protease gene selected from the group consisting of PEP4 and PBR1;

Embodiment 22: Method according to embodiment 8, wherein the yeast strain has a further non-functional protease gene selected from the group consisting of PEP4 and STE13;

Embodiment 23: Method according to embodiment 8, wherein the yeast strain has a further non-functional protease gene selected from the group consisting of PEP4 and KEX2;

Embodiment 24: Method according to embodiment 8, wherein the yeast strain has a further non-functional protease gene selected from the group consisting of YPS3 and YPS5;

Embodiment 25: Method according to embodiment 8, wherein the yeast strain has a further non-functional protease gene selected from the group consisting of YPS3 and YPS6;

Embodiment 26: Method according to embodiment 8, wherein the yeast strain has a further non-functional protease gene selected from the group consisting of YPS3 and YPS7;

Embodiment 27: Method according to embodiment 8, wherein the yeast strain has a further non-functional protease gene selected from the group consisting of YPS3 and PBR1;

Embodiment 28: Method according to embodiment 8, wherein the yeast strain has a further non-functional protease gene selected from the group consisting of YPS3 and STE13;

Embodiment 29: Method according to embodiment 8, wherein the yeast strain has a further non-functional protease gene selected from the group consisting of YPS3 and KEX2;

Embodiment 30: Method according to embodiment 8, wherein the yeast strain has a further non-functional protease gene selected from the group consisting of YPS1 and PBR1;

Embodiment 31: Method according to embodiment 8, wherein the yeast strain has a further non-functional protease gene selected from the group consisting of YPS1 and STE13;

Embodiment 32: Method according to embodiment 8, wherein the yeast strain has a further non-functional protease gene selected from the group consisting of YPS1 and KEX2;

Embodiment 33: Method according to embodiment 1, wherein the yeast strain has a nonfunctional KEX1 gene and a non-functional PEP4 gene;

Embodiment 34: Method according to embodiment 1, wherein the yeast strain has a nonfunctional KEX1 gene and a non-functional YPS1 gene;

Embodiment 35: Method according to embodiment 1, wherein the yeast strain has a nonfunctional KEX1 gene and a non-functional MKC7 gene;

Embodiment 36: Method according to embodiment 1, wherein the yeast strain has a nonfunctional KEX1 gene and a non-functional YPS3 gene;

Embodiment 37: Method according to embodiment 1, wherein the yeast strain has a nonfunctional KEX1 gene and a non-functional YPS5 gene;

Embodiment 38: Method according to embodiment 1, wherein the yeast strain has a nonfunctional KEX1 gene and a non-functional YPS6 gene;

Embodiment 39: Method according to embodiment 1, wherein the yeast strain has a nonfunctional KEX1 gene and a non-functional YPS7 gene;

Embodiment 40: Method according to embodiment 1, wherein the yeast strain has a nonfunctional KEX1 gene and a non-functional PBR1 gene;

Embodiment 41: Method according to embodiment 1, wherein the yeast strain has a nonfunctional KEX1 gene and a non-functional STE13 gene;

Embodiment 42: Method according to embodiment 1, wherein the yeast strain has a nonfunctional KEX1 gene and a non-functional KEX2 gene;

Embodiment 43: Method according to embodiment 1, wherein the yeast strain has a knockout of the KEX1 gene and a single of the protease genes selected from the following group PEP4, YPS1, MKC7(YPS2), YPS3(YPS4), YPS5, YPS6, YPS7, PRB1, STE13 and KEX2;

Embodiment 44: Method according to embodiment 1, wherein the yeast strain has a knockout of the KEX1 gene and two of the protease genes selected from the following group PEP4, YPS1, MKC7(YPS2), YPS3(YPS4), YPS5, YPS6, YPS7, PRB1, STE13 and KEX2;

Embodiment 45: Method according to embodiment 1, wherein the yeast strain has a knock-out of the KEX1 gene and three of the protease genes selected from the following group PEP4, YPS1, MKC7(YPS2), YPS3(YPS4), YPS5, YPS6, YPS7, PRB1, STE13 and KEX;

Embodiment 46: Method according to embodiment 1, wherein yeast strain has a knock-out of the KEX1 gene and four of the protease genes selected from the following group PEP4, YPS1, MKC7(YPS2), YPS3(YPS4), YPS5, YPS6, YPS7, PRB1, STE13 and KEX2;

Embodiment 47: Method according to any of the previous embodiments, wherein the KEX1 gene has been deleted;

Embodiment 48: Method according to any of previous embodiments, wherein the KEX1 gene has been made non functional by mutation, e.g. by homologous recombination;

Embodiment 49: Method according to any of the previous embodiments, wherein polypeptide has from 25 to about 45 amino acid residues in the backbone;

Embodiment 50: Method according to any of the previous embodiments, wherein polypeptide is selected from the group consisting of amylin, amylin analogues, PP and PP analogues, PYY and PYY analogues, GLP-1 and GLP1 analogues, oxytocin, vasopressin, calcitonin, gastrin, NPY, FMRF amide, secretin, GFHR, CRF, neurokinin A, gastrin releasing peptide and α-MSH;

Embodiment 51: Method according to embodiment 50, wherein polypeptide is selected from the group consisting of PP, PYY and amylin;

Embodiment 52: Method according to embodiment 50, wherein polypeptide is amylin;

Embodiment 53: Method according to embodiment 50, wherein polypeptide is PP;

Embodiment 54: Method according to embodiment 50, wherein polypeptide is PYY;

The invention covers any combination of embodiments and aspects as described herein.

EXAMPLES

General Procedures

All expressions plasmids are of the C-POT type, similar to those described in EP 171,142. These are 2μ-based expression vectors characterized by containing the *Schizosaccharomyces pombe* triose phosphate isomerase gene (POT) for the purpose of plasmid selection and stabilization in *S. cerevisiae*. The plasmids also contain the *S. cerevisiae* triose phosphate isomerase promoter and terminator. These sequences are similar to the corresponding sequences in plasmid pKFN1003 (described in WO 9010075). In order to facilitate cloning of different fusion proteins the DNA sequence encoding the MFα1 pre-pro leader has been changed to incorporate a NcoI site and is called the MFα1* pre-pro leader. Thus the NcoI-XbaI fragment is simply replaced by an NcoI-XbaI fragment encoding the insulin construct of interest. Such NcoI-XbaI fragments may be synthesized using synthetic oligonucleotides and PCR according to standard techniques. In addition to the alpha-leader other leaders can be used.

Yeast transformants and derivatives thereof were prepared by transformation of the host strains S. cerevisiae strain. The yeast strains were grown on YPGaL (1% Bacto yeast extract, 2% Bacto peptone, 2% galactose, 1% lactate) to an O.D. at 600 nm of 0.6. 100 ml of culture was harvested by centrifugation, washed with 10 ml of water, recentrifuged and resuspended in 10 ml of a solution containing 1.2 M sorbitol, 25 mM Na$_2$EDTA pH=8.0 and 6.7 mglml dithiotreitol. The suspension was incubated at 30° C. for 15 minutes, centrifuged and the cells resuspended in 10 ml of a solution containing 1.2 M sorbitol, 10 mM Na$_2$EDTA. 0.1 M sodium citrate, pH 0 5.8, and 2 mg NovozymC3234. The suspension was incubated at 30° C. for 30 minutes, the cells collected by centrifugation, washed in 10 ml of 1.2 M sorbitol and 10 ml of CAS (1.2 M sorbitol, 10 mM CaCl$_2$, 10 mM Tris HCl (Tris=Tris(hydroxymethyl)-aminomethane) pH=7.5) and resuspended in 2 ml of CAS. For transformation, 1 ml of CAS-suspended cells was mixed with approx. 0.1 mg of plasmid DNA and left at room temperature for 15 minutes. 1 ml of (20% polyethylene glycol 4000, 10 mM CaCl$_2$, 10 mM Tris HCl, pH=7.5) was added and the mixture left for a further 30 minutes at room temperature. The mixture was centrifuged and the pellet resuspended in 0.1 ml of SOS (1.2 M sorbitol, 33% v/v YPD, 6.7 mM CaCl$_2$) and incubated at 30° C. for 2 hours. The suspension was then centrifuged and the pellet resuspended in 0.5 ml of 1.2 M sorbitol. Then, 6 ml of top agar (the SC medium of Sherman et al. (1982) Methods in Yeast Genetics, Cold Spring Harbor Laboratory) containing 1.2 M sorbitol plus 2.5% agar) at 52° C. was added and the suspension poured on top of plates containing the same agar-solidified, sorbitol containing medium.

Example 1

Δkex1::TRP1-ΔFA Gene Disruption
The trp1-ΔFA deletion allele mutation was constructed as follows:

A synthetic DNA fragment encoding the trp1-ΔFA allele was synthesized by PCR using synthetic oligonucleotides (Horecka J, Jigami Y. (1999). The trp1-ΔFA designer deletion for PCR-based gene functional analysis in Saccharomyces cerevisiae. Yeast.: 15 (1769-74)) and standard techniques.

The trp1-ΔFA fragment is composed of a 476 by fragment from the KEX15'UTR region directly fused to a 525 by fragment from the KEX1 3'UTR region thus avoiding homologous DNA sequence overlap to the TRP1-FA cassette used as selectable marker in the pFA6a-TRP1 plasmid (Longtine, M. S., McKenzie, A., Demarini, D., Shah, N. G., Wach, A., Brachat, A., Philippsen, P. and Pringle, J. R. (1998). Additional modules for versatile and economical PCR-based gene deletion and modification in Saccharomyces cerevisiae. Yeast: 14., (953-961)).The trp1-ΔFA PCR fragment was cloned into the TOPO-CR2.1 vector as described by the manufacturer (Invitrogen) resulting in plasmid pFI379
A trp1-ΔFA deletion yeast strain was obtained as follows:
The method used to select for disruption of the TRP1 gene involves a counter selection procedure were growth on media containing 5-fluoroanthranilic acid results in antimetabolism by the enzymes in the tryptophan biosynthetic pathway. Yeast cells, which lack the enzymes required for the conversion of anthranilic acid to tryptophan, are resistant to 5fluoroanthranilic acid (Toyn, J. H., Gunyuzlu, P. L., White, H., Thompson, L. A. and G. F. Hollis (2000). A counterselection for the tryptophan pathway in yeast: 5-fluoroanthranilic acid resistance. Yeast: 16 (553-560)).

Yeast host strain NNY574 (MATαura3-D1 leu2-D1 his3-D0 toi1::URA3 yps1::HIS3 pep4::LEU2) was transformed with plasmid pSA281, a yeast expression vector for secretory expression of an amylin analogue precursor EEAEK(SEQ ID NO:1)-amylin (1-37)-K1E, S28P, S29P, G38 to create yFI754. The plasmid backbone of pSA281 is based on the cPOT type vector facilitating growth in rich media containing glucose as sole carbon source by complementation of the delta-tpil mutation of the host strain.

A trp1-ΔFA fragment was amplified by PCR using pFI379 as template and synthetic oligonucleotides and standard methods. The trp1-ΔFA PCR fragment was used directly for transformation of yFI754 by the LiAc method (Gietz and Wood, 2002). After transformation, the yeast cells were plated on YEPD agar and incubated overnight at 30° C. followed by replicaplating onto minimal containing 5-fluoroanthranilic acid. Selection for yeast cells with the trp1-ΔFA deletion allele integrated into the genome was done by counter selection for the presence of the TRP1 gene using 5-fluoroanthranilic acid (Toyn et al, 2000) resulting in the trp1-ΔFA yeast strain yFI810.
The Δkex1::TRP1-FA gene disruption allele was constructed as follows:

A synthetic DNA fragment of the Δkex1-D1 allele composed of 518 by of the KEX1 5'UTR DNA sequence followed by a SphI restriction endonuclease site followed by a Sbf1 restriction endonuclease site followed by 304 by of the KEX1 3'UTR DNA sequence was constructed by in vitro DNA synthesis from a commercial source and obtained cloned into a pMA vector (Geneart AG, BioPark, Josef-Engert-Str. 11, D-93053 Regensburg, Germany). This plasmid was named pFI472. A synthetic DNA fragment containing the TRP1-FA cassette flanked by SphI and Sbf1 restriction endonuclease sites was constructed by in vitro DNA synthesis from a commercial source and obtained cloned into a pMA-RQ vector (GeneArt ag). This plasmid was named pFI468. A plasmid, pFI473, containing the Δkex1::TRP1-FA gene disruption allele was constructed by ligation of two DNA fragments: A 3163 by fragment obtained after digestion of pFI472 with SphI and Sbf1 and a 872 by fragment obtained after digestion of pFI468 with SphI and Sbfl. Finally, pFI473 was digested with XhoI and HincII and a 1707 by DNA fragment containing the Δkex1::TRP1-FA allele was isolated and used for transformation of yFI810 by the LiAc procedure (Gietz, R. D. and Wood, R. (2002). Transformation of yeast by lithium acetate/single-stranded carrier DNA/polyethylene glycol method. Methods in Enzymology: 350, (87-96)). After transformation, the yeast cells were plated onto minimal plates without tryptophan in order to select for Δkex1::TRP1-FA deletion mutants. TRP+ transformants wer characterized by PCR to confirm correct integration of Δkex1::TRP1-FA allele into the KEX1 locus. Yeast strain yFI815 was isolated as a Δkex1::TRP1-FA deletion mutant (MATα ura3-D0 leu2-D0 his3-D0 trp1-delta-FA tpi1::URA3 yps1::HIS3 pep4::LEU2 kex1::TRP1-FA, pSA281).

Example 2

Δkex1::KanMX4 Gene Disruption
A yeast strain with the KEX1 gene deleted and the genotype Math his3D1 leu2D0 lys2D0 ura3D0 kex1D0::kanMX4, was purchased from the Euroscarf deletion strain collection (Acc. no. Y14570). In this yeast strain, the DNA fragment encoding the KEX1 open reading frame has been replaced with the KanMX4 dominant selectable marker, conferring resistance to the antibiotic G418/geneticin (Wach A., Brachat, A., Pöelmann R. and Philippsen, P. (1994). New heterologous modules for classical or PCR-based gene disruptions in Saccharomyces cerevisiae. Yeast: 10 (1793-808).

Genomic DNA was isolated from Y14570 and used as template in a standard PCR reaction with synthetic oligonucleotides oTKLH68 (cccggaaccgaaaaacaatgtgga) (SEQ ID NO:2) and oILLa482 (agttcagtagtgtgaattaaataaaacagtcagttcttgatggattgtacccfttaaagaatttatctttatg) (SEQ ID NO:3) in order to amplify a synthetic DNA fragment containing the Δkex1::KANMX4 deletion allele cassette. This DNA fragment was used directly for transformation of yFI650 (host strain NNY574 with cPOT plasmid pSA082) by the LiAc method (Gietz, R. D. and Wood, R. (2002). Transformation of yeast by lithium acetate/single-stranded carrier DNA/polyethylene glycol method. Methods in Enzymology: 350, (87-96)). After transformation, the yeast cells were plated on YEPD agar and incubated overnight at 30° C. followed by replicaplating onto selective YEPD agar +200 mg/L G418. Yeast colonies appearing after 3 days further incubation at 30° C. were isolated and characterized by PCR to confirm the correct integration of Δkex1::KanMX4 allele into the KEX1 locus. Yeast strain yFI750 was isolated as a Δkex1::KanMX4 deletion mutant (MATα ura3-D0 leu2-D0 his3-D0 trp1-delta-FA tpi1::URA3 yps1::HIS3 pep4::LEU2 kex1::KanMX4, pSA082). Removal of cPOT plasmid from yFI750 was induced by growing for many generations without glucose selection. The resulting yeast strain, yFI751 (MATα ura3-D0 leu2-D0 his3-D0 trp1-delta-FA tpi1::URA3 yps1::HIS3 pep4::LEU2 kex1::KanMX4) was used as new host strain for transformation with yeast expression vectors of the cPOT type.

Example 3

LC-MS analysis using a LC/MSD TOF instrument (Agilent) was used to determine the molecular mass of secreted peptides in yeast supernatants according to the settings recommended by the manufacturer. Deconvolution of the TIC chromatogram was done using the accompanying software. The abundances of full-length and glycin-deleted species was obtained from the deconvoluted spectrum and used for estimation of the percentage of fulllength peptide vs the pool of full-length and glycine-deleted peptide (table 1).

TABLE 1

| | Host | | | | | |
|---|---|---|---|---|---|---|
| | NNY574 KEX1 | | | yFI751 (according to the invention) Δkex1 | | |
| Secreted peptide | Plasmid | Strain | % Full-length | Plasmid | Strain | % Full-length |
| N terminally extended_amylin (1-37) K1E, S28P, S29P, G38 | pSA281 | yFI754 | 64 | pSA281 | yFI797 | 95 |
| PP (1-36) K26 G37 | pSA328 | yFI757 | 44 | pSA328 | yFI798 | 97 |

It appears from Table 1 that expression of polypeptides with a C-terminal glycine in a strain having a deleted (non-functional) KEX1 gene approximately double the expression of full length product.

Example 4

Construction of yeast expression systems and production of EEAEK-amylin (1-37) K1E, S28P, S29P, G38

Figure 1:
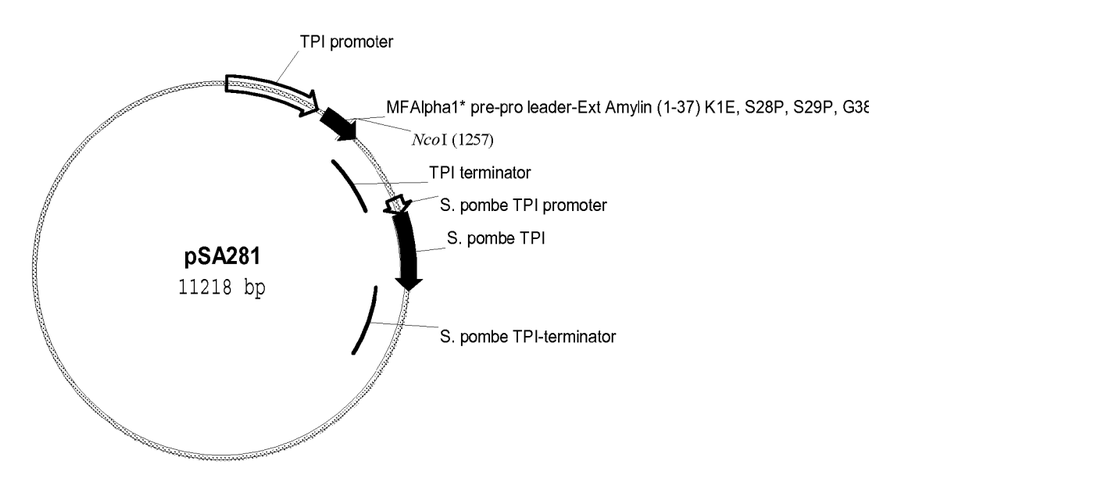
FIG. 1 illustrates the construction of yeast expression systems.

Expressions plasmids are of the C-POT type, similar to those described in EP 171,142. These are 2μ-based expression vectors characterized by containing the *Schizosaccharomyces pombe* triose phosphate isomerase gene (POT) for the purpose of plasmid selection and stabilization in *S. cerevisiae*. The plasmids also contain the *S. cerevisiae* triose phosphate isomerase promoter and terminator. These sequences are similar to the corresponding sequences in plasmid pKFN1003 (described in WO 90100075) as are all other sequences except the following: 1) The sequence of the EcoRI-XbaI fragment encoding the fusion protein of the leader and the insulin product. 2) A silent mutation has been introduced resulting in removal of a NcoI-site in the 2μ-region in the expression vector. In order to facilitate cloning of different fusion proteins the DNA sequence encoding the MFα1 pre-pro leader has been changed to incorporate a NcoI site (see FIG. 1) and is called the MFα1* pre-pro leader. Thus the NcoI-XbaI fragment is simply replaced by an NcoI-XbaI fragment encoding the precursor molecule of interest. Such NcoI-XbaI fragments may be constructed synthetically or synthesized using synthetic oligonucleotides and PCR according to standard techniques. In addition to the alpha-leader other leaders can be used. A synthetic DNA fragment containing sequences encoding EEAEAK-amylin (1-37) K1E, S28P, S29P, G38 was obtained form Geneart AG, Bio-Park, Josef-Engert-Str. 11, D-93053 Regensburg, Germany. The synthetic amylin (1-37) K1E, S28P, S29P, G38 was furnished with 5' DNA sequences encoding an N-terminal extension EEAEK (SEQ ID NO:1) to facilitate expression in yeast. The synthetic DNA was digested with NcoI and XbaI and ligated to the NcoI-XbaI vector fragment of the modified cPOT type expression vector (FIG. 1). This resulted in expression plasmid pSA281 encoding EEAEK-amylin (1-37) K1E, S28P, S29P, G38 with the sequence EEAEKCNTATCATQRLANFLVHSSNNFGPILPPTNVGSNTYG (SEQ ID NO: 4). The DNA sequence has the following sequence: gaagaagctgaaaaagaatgtaatactgctacttgtgctactcaaagattg-gctaattttttggttcattcttctaataattttggtccaat tttgccaccaactaatgttg-gttctaatacttatggt (SEQ ID N0:5).

The expression plasmid was propagated in *E. coli*, grown in the presence of ampicillin and isolated using standard techniques (Sambrook et al., 1989). The plasmid DNA was checked for insert by appropriate restriction nucleases (e.g. EcoRI, NcoI, XbaI) and was shown by sequence analysis to contain the proper sequence of the Ext Amylin (1-37) K1E, S28P, S29P, G38.

The plasmid was transformed into *S. cerevisiae* strains NNY547 and yFI751. Yeast transformants harbouring the plasmid were selected by glucose utilization as carbon source on YPD (1% yeast extract, 2% peptone, 2% glucose) agar (2%) plates. The resulting yeast strains were inoculated into 5 ml of growth media containing glucose as the sole carbon source. The cultivation was carried out at 30° C. for 3 days. After centrifugation the supernatant was removed for LC/MS analysis by which method the identity of secreted molecules wer confirmed as described above.

Example 5

Construction of Yeast Expression Systems and Production of PP Analogue Precursor Molecule PP(1-36) K26 G37

Synthetic DNA fragments containing sequence encoding PP(1-36) K26, G37 and was obtained form Geneart AG, BioPark, Josef-Engert-Str. 11, D-93053 Regensburg, Germany. The synthetic DNA was digested with NcoI and XbaI and ligated to the NcoI-XbaI vector fragment of the modified cPOT type expression vector (FIG. 1). This resulted in expression plasmid pSA228 encoding PP(1-36) K26 G37 with the following amino acid sequence APLEPVYPGD-NATPEQMAQYAADLRKYINMLTRPRYG (SEQ ID NO:6). The corresponding DNA sequence is as follows:

(SEQ ID NO: 7)
```
gcaccattggaaccagtttacccaggtgataacgcaactccagagcagatggctcagtatgctgcagatttaagaaagtatataa
atatgttaacaagaccaagatatggt.
```

The identity of the expression vector was verified, the plasmid was transformed into *S. cerevisiae* and the yeast strain was grown and secreted protein harvested as described above.

Example 6

Construction of Yeast Expression Systems and Production of EEAEK-amylin (1-37) K1E, S28P, S29P, X37, G38

To examine the effect of the identity of the amino acid next to the C-terminal glycine residue synthetic DNA fragments containing sequence encoding EEAEK-amylin (1-37) K1E, S28P, S29P, X37, G38 where the amino acid residue (amino acid residue No. 37) attached to the C-terminal Gly is A, G, F, I, M, S, P, T, W, R, L, Q or N were obtained form Geneart AG, BioPark, Josef-Engert-Str. 11, D-93053 Regensburg, Germany. The synthetic DNA was digested with NcoI and XbaI and ligated to the NcoI-XbaI vector fragment of the modified cPOT type expression vector (FIG. 1).

This resulted in expression plasmids encoding EEAEKCNTATCATQRLANFLVHSSNNFG-PILPPTNVGSNTAG (SEQ ID NO:8), EEAEKCNTATCATQRLANFLVHSSNNFGPILPPTNVGSNTGG (SEQ ID NO:9), EEAEKCNTATCATQRLANFLVHSSNNFG-PILPPTNVGSNTFG (SEQ ID NO:10), EEAEKCNTATCATQRLANFLVHSSNNFGPILPPTNVGSNTIG (SEQ ID NO:11), EEAEKCNTATCATQRLANFLVHSSNNFG-PILPPTNVGSNTMG (SEQ ID NO 12), EEAEKCNTATCATQRLANFLVHSSNNFGPILPPTNVGSNTSG (SEQ ID NO:13), EEAEKCNTATCATQRLANFLVHSSNNFG-PILPPTNVGSNTPG (SEQ ID NO:14), EEAEKCNTATCATQRLANFLVHSSNNFGPILPPTNVGSNTTG (SEQ ID NO:15), EEAEKCNTATCATQRLANFLVHSSNNFG-PILPPTNVGSNTWG (SEQ ID NO:16), EEAEKCNTATCATQRLANFLVHSSNNFGPILPPTNVGSNTRG (SEQ ID NO:17), EEAEKCNTATCATQRLANFLVHSSNNFG-PILPPTNVGSNTLG (SEQ ID NO:18), EEAEKCNTATCATQRLANFLVHSSNNFGPILPPTNVGSNTQG (SEQ ID NO:19) and EEAEKCNTATCATQRLANFLVHSSNNFG-PILPPTNVGSNTNG (SEQ ID NO:20), The corresponding DNA sequences are as follows:

(SEQ ID NO: 21)
```
gaagaagctgaaaaagaatgtaatactgctacttgtgctactcaaagattggctaattttttggttcattcttctaataattttggtccaat
tttgccaccaactaatgttggttctaatactgctggt;
```

(SEQ ID NO: 22)
```
gaagaagctgaaaaagaatgtaatactgctacttgtgctactcaaagattggctaattttttggttcattcttctaataattttggtccaat
tttgccaccaactaatgttggttctaatactggtggt;
```

(SEQ ID NO: 23)
```
gaagaagctgaaaaagaatgtaatactgctacttgtgctactcaaagattggctaattttttggttcattcttctaataattttggtccaat
tttgccaccaactaatgttggttctaatacttttggt;
```

(SEQ ID NO: 24)
```
gaagaagctgaaaaagaatgtaatactgctacttgtgctactcaaagattggctaattttttggttcattcttctaataattttggtccaat
tttgccaccaactaatgttggttctaatactattggt;
```

(SEQ ID NO: 25)
```
gaagaagctgaaaaagaatgtaatactgctacttgtgctactcaaagattggctaattttttggttcattcttctaataattttggtccaat
tttgccaccaactaatgttggttctaatactatgggt;
```

(SEQ ID NO: 26)
```
gaagaagctgaaaaagaatgtaatactgctacttgtgctactcaaagattggctaattttttggttcattcttctaataattttggtccaat
tttgccaccaactaatgttggttctaatacttctggt;
```

(SEQ ID NO: 27)
```
gaagaagctgaaaaagaatgtaatactgctacttgtgctactcaaagattggctaattttttggttcattcttctaataattttggtccaat
tttgccaccaactaatgttggttctaatactcctggt;
```

(SEQ ID NO: 28)
```
gaagaagctgaaaaagaatgtaatactgctacttgtgctactcaaagattggctaattttttggttcattcttctaataattttggtccaat
tttgccaccaactaatgttggttctaatactactggt;
```

(SEQ ID NO: 29)
```
gaagaagctgaaaaagaatgtaatactgctacttgtgctactcaaagattggctaattttttggttcattcttctaataattttggtccaat
tttgccaccaactaatgttggttctaatacttggggt;
```

-continued (SEQ ID NO: 30)
gaagaagctgaaaaagaatgtaatactgctacttgtgctactcaaagattggctaattttttggttcattcttctaataattttggtccaat tttgccaccaactaatgttggttctaatactagaggt;

(SEQ ID NO: 31)
gaagaagctgaaaaagaatgtaatactgctacttgtgctactcaaagattggctaattttttggttcattcttctaataattttggtccaat tttgccaccaactaatgttggttctaatactcttggt;

(SEQ ID NO: 32)
gaagaagctgaaaaagaatgtaatactgctacttgtgctactcaaagattggctaattttttggttcattcttctaataattttggtccaat tttgccaccaactaatgttggttctaatactcaaggt
and (SEQ ID NO: 33)
gaagaagctgaaaaagaatgtaatactgctacttgtgctactcaaagattggctaattttttggttcattcttctaataattttggtccaat tttgccaccaactaatgttggttctaatactaatggt.

The identity of the expression vector was verified, the plasmid was transformed into *S. cerevisiae* and the yeast strain was grown and secreted protein harvested and analysed as described above in example 3 and 4 The abundances of full-length and glycine-deleted species was obtained from the deconvoluted spectra and used for estimation of the percentage of full-length peptide vs the pool of full-length and glycine-deleted peptide. The results appear from Table 2. It appears from Table 2 that the C-terminal Gly in the amylin molecule is cleaved off when the amino acid residue attached to the Gly is one of Tyr, Phe, Met, Leu, Trp, Ala, Ile and Arg.

TABLE 2

| Amino acid next to Gly (X37) | % Full-length |
|---|---|
| Tyr | 45.5 |
| Phe | 47.6 |

TABLE 2-continued

| Amino acid next to Gly (X37) | % Full-length |
|---|---|
| Met | 60.6 |
| Leu | 74.4 |
| Trp | 85.3 |
| Ala | 85.6 |
| Ile | 87.6 |
| Arg | 94.1 |
| Gly | 100 |
| Ser | 100 |
| Pro | 100 |
| Asn | 100 |
| Thr | 100 |
| Gln | 100 |

The invention claimed is:

1. A method for making a polypeptide in a yeast strain having a nonfunctional KEX1 gene, wherein, the polypeptide as its C-terminal amino acid residue has a glycine, and wherein the method comprises the following steps:
   a) culturing the yeast strain comprising a DNA sequence encoding the polypeptide under conditions for expressing the polypeptide in the yeast strain and
   b) isolating the expressed polypeptide.

2. The method according to claim 1, wherein the polypeptide is isolated from the culture medium.

3. The method according to claim 1, wherein the amino acid residue attached to the C-terminal Gly is selected from the group consisting of Tyr, Phe, Met, Leu, Trp, Ala, Ile, Val, and Arg.

4. The method according to claim 3, wherein the amino acid residue attached to the C-terminal Gly is selected from the group consisting of Val, Leu, Ile, and Met.

5. The method according to claim 3, wherein the amino acid residue attached to the C-terminal Gly is selected from the group consisting of Tyr, Trp, and Phe.

6. The method according to claim 1, wherein the yeast strain has at least one further non-functional protease gene selected from the group consisting of PEP4, YPS1, MKC7, YPS3, YPS5, YPS6, YPS7, PRB1, STE13 and KEX2.

7. The method according to claim 6, wherein the yeast strain has a further non-functional protease gene selected from the group consisting of PEP4 and YPS1.

8. The method according to claim 6, wherein the yeast strain has a further non-functional protease gene selected from the group consisting of PEP4 and YPS3.

9. The method according to claim 6, wherein the yeast strain has a further non-functional protease gene selected from the group consisting of PEP4 and MKC7.

10. The method according to claim 6, wherein the yeast strain has a further non-functional protease gene selected from the group consisting of YPS3 and YPS1.

11. The method according to claim 6, wherein the yeast strain has a further non-functional protease gene selected from the group consisting of YPS3 and MKC7.

12. The method according to claim 1, wherein the polypeptide is selected from the group consisting of amylin and amylin analogues, PP (pancreatic polypeptide) and PP analogues, PYY (peptide tyrosine tyrosine) and PYY analogues, GLP-1(Glucagon-like peptide-1) and GLP1 analogues, oxytocin, vasopressin, calcitonin, gastrin, NPY (neuropeptide Y), FMRF amide (Phe-Met-Arg-Phe), secretin, GFHR (growth factor hormone receptor), CRF (corticotropin-releasing factor), neurokinin A, gastrin releasing peptide, and α-MSH (alpha-melanocyte-stimulating hormone).

13. The method according to claim 12, wherein the polypeptide is selected from the group consisting of PP, PYY, and amylin.

14. The method according to claim 12, wherein the polypeptide is amylin.

15. The method according to claim 12, wherein the polypeptide is PP.

16. The method according to claim 12, wherein the polypeptide is PYY.

* * * * *